United States Patent [19]

Zanelli et al.

[11] Patent Number: 4,781,912
[45] Date of Patent: Nov. 1, 1988

[54] CATIONIC COMPLEX OF TECHNETIUM-99M.

[75] Inventors: Giuseppe D. Zanelli; Frank Brady; Niranjan M. Patel; Avijit Lahiri, all of Harrow, United Kingdom

[73] Assignee: Mallinckrodt, Inc., St. Louis, Mo.

[21] Appl. No.: 941,917

[22] Filed: Dec. 15, 1986

[30] Foreign Application Priority Data

Dec. 19, 1985 [GB] United Kingdom ............... 8531296

[51] Int. Cl.$^4$ ................ A61K 49/02; C07F 13/00
[52] U.S. Cl. .................................... 424/1.1; 534/14
[58] Field of Search ........................... 424/1.1; 534/14

[56] References Cited

U.S. PATENT DOCUMENTS

| | | | |
|---|---|---|---|
| 4,374,821 | 2/1983 | Glavan et al. | 424/1.1 |
| 4,419,339 | 12/1983 | Neirinckx | 424/1.1 |
| 4,452,774 | 6/1984 | Jones et al. | 424/1.1 |
| 4,481,184 | 11/1984 | Kronauge et al. | 424/1.1 |
| 4,489,054 | 12/1984 | Deutsch et al. | 424/1.1 |
| 4,707,544 | 11/1987 | Jones et al. | 424/1.1 X |

OTHER PUBLICATIONS

Zanelli et al., "Cationic Complex . . . For Imaging,"
Europ. Pat. Appln., 226,259, Jun. 24, 1987, [CA. 107;194297y].

Primary Examiner—John F. Terapane
Assistant Examiner—John S. Maples
Attorney, Agent, or Firm—R. J. Klostermann; L. N. Goodwin

[57] ABSTRACT

The invention relates to a cationic complex of technetium-99m with (a) at least one bidendate ligand X having the formula

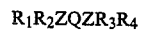

$$R_1R_2ZQZR_3R_4$$

where
each Z is phosphorus or arsenic,
Q is a $(CH_2)_n$ linking group where n is 2 to 8 or a 1,2-phenylene linking group,
each of $R_1$, $R_2$, $R_3$ and $R_4$ is hydrogen, $C_1$ to $C_5$ alkyl or phenyl; and (b) at least one monodentate isonitrile ligand Y.

The invention also relates to a radiopharmaceutical composition comprising said complex, to a kit for preparing said composition, and to the use of said composition for a radiodiagnostic examination.

7 Claims, No Drawings

CATIONIC COMPLEX OF TECHNETIUM-99M.

The invention relates to a cationic complex of technetium-99m, as well as to a process for preparing said complex. The invention also relates to a radiopharmaceutical composition comprising said complex, to a kit for preparing said composition, and to the use of said composition for a radiodiagnostic examination.

Radionuclide-labelled compounds are used for diagnostic examination, e.g. into deviations in shape and function of internal organs and into the presence and location of pathological processes in the body. For this purpose, a preparation in which the radioactive compound is present in administered to the patient, for example, in the form of an injectable liquid. By means of suitable detectors, e.g. a gamma camera, images can be obtained by recording the emitted radiation, of, for example, the organ or the pathological process in which the radioactive compound has been incorporated.

In the description hereinafter the following abbreviations have been used:
Technetium-99m—Tc-99m
1,2-dimethylphosphinoethane—DMPE
1,2-diethylphosphinoethane—DEPE
tert-butylisonitrile—t-BuNC U.S. Pat. No. 4,374,821 describes myocardial imaging agents of the general type $[Tc\text{-}99m(DEPE)_2O_2]^+A^-$ and $[Tc\text{-}99m(DMPE)_2O_2]^+A^-$, where A is an anion. The biodistribution properties of the compounds, however, are not described.

U.S. Pat. No. 4,419,339 describes cationic lipophilic complexes of technetium-99m that are useful as negative heart imaging agents having the formula $[Tc\text{-}99m(DEPE)_2Cl_2]^+Cl^-$ and $[Tc\text{-}99m(DMPE)_2Cl_2]^+Cl^-$. Again, the biodistribution properties of the complexes are not described.

U.S. Pat. No. 4,452,774 describes complexes of the kind $[Tc\text{-}99m(t\text{-}BuNC)_6]^+$. The complexes are stated to be useful as labelling and imaging agents. The animal tests reported suggest that, on injection into animals, the complexes are located in the lungs.

U.S. Pat. No. 4,489,054 describes cationic lipophilic complexes of Tc-99m, such as $[Tc\text{-}99m(DMPE)_2Cl_2]^+Cl^-$, for hepatobiliary and myocardial imaging.

The present invention provides a cationic lipophilic complex of technetium-99m with:
(a) at least one bidendate ligand X having the formula $R_1R_2ZQZR_3R_4$ where
each Z is phosphorus or arsenic,
Q is a $(CH_2)_n$ linking group where n is 2 to 8 or a 1,2-phenylene linking group,
each of $R_1$, $R_2$, $R_3$ and $R_4$ is hydrogen, $C_1$ to $C_5$ alkyl or phenyl; and
(b) at least one monodentate isonitrile ligand Y.

The structures of the complexes of the present invention are not known with certainty. Various structures involving one Tc-99m atom can be envisaged, including:

$[Tc\text{-}99m\ X_2Y_2]^+$ (i)

$[Tc\text{-}99m\ X_2YO]^+$ (ii)

$[Tc\text{-}99m\ X_2YA]^+$ (iii)

$[Tc\text{-}99m\ XY_4]^+$ (iv)

(wherein A is an anion).

Other complex structures envisaged include two or more Tc-99m atoms. It is presently believed that the products of the preparative reactions are or include complexes of structure (i).

Preferably Z is phosphorus, Q is $(CH_2)_2$ and $R_1$, $R_2$, $R_3$ and $R_4$ are all the same and are all methyl or ethyl. Preferably Y is a hydrocarbon isonitrile, such as isopropyl, tert.-butyl, cyclohexyl or 1,1,3-tetramethylbutyl isonitrile, tosylmethyl isonitrile or benzyl isonitrile. The nature of the anion $A^-$ is not critical; $A^-$ may for example be $Cl^-$.

The cationic complexes of the invention may be prepared from the corresponding complexes $(Tc\text{-}99m\ X_2O_2)^+$. A mixture of this complex with the appropriate mono-isonitrile may be refluxed under an inert gas in the presence of a reducing agent such as sodium dithionite. The pH is preferably kept in the range 3 to 6, as a mixture of products may be formed if the pH is too low. It is preferred to perform this reduction in the presence of an anti-oxidant such as p-aminobenzoic acid (PABA) which appears to suppress the formation of unwanted impurities. The complex may be recovered by passing the reaction mixture through a silica filter cartridge (which adsorbs the desired complex) and eluted with ethanol. The complex may be further purified by means of an anion exchange resin. The starting complexes $(Tc\text{-}99m\ X_2O_2)^+$ for the above preparation process are known compounds described in the aforesaid U.S. Pat. No. 4,374,821. They may be prepared by a reaction of complexes of the kind $(FeX_2Cl_2)^+Cl^-$ with generator eluate pertechnetate. The reaction is preferably performed under rather mild conditions, for example 15 minutes at 100° C., as more vigorous conditions can give rise to the formation of undesired products. Thus, for example, refluxing the reaction mixture for 30 minutes at 140° C. can produce $(Tc\text{-}99m\ X_3)^+Cl^-$; and heating the reaction mixture for 1 hour in a sealed vial at 140° C. can produce $(Tc\text{-}99m\ X_2Cl_2)^+Cl^-$.

Preferably, however, the cationic complexes of the present invention are prepared by reacting corresponding non-radioactive metal ion comprising complexes with technetium-99m in the form of a pertechnetate in the presence of a reducing agent and, if desired, one or more auxiliary substances, or, alternatively, by reacting non-radioactive metal ion comprising complexes including oxo or halo ligands with an isonitrile in the presence of a base and with technetium-99m under the above conditions. In principle all complex-forming metal ions are suitable as non-radioactive metal ions for the starting cationic complexes, such as ions for Tc, Ru, Co, Pt, Fe, Os, Ir, W, Re, Cr, Mo, Mn, Ni, Rh, Pd, Ta and the like.

It has surprisingly been found, that the cationic complexes of the present invention, after having been injected intravenously into human beings, are strongly (approx. 100%) bound to plasma proteins and circulate in the bloodstream for a long period of time without substantially being removed therefrom. The half-life of the complexes in the bloodstream is approx. 4.4 hours, which is comparable to the half-life of technetium-99m per se. This is completely beyond expectation, because the complexes known from the before-mentioned U.S. patents can be used for organ imaging, in particular myocardial imaging, and consequently are removed relatively fast from the bloodstream to be taken up into the organs. On the contrary, the complexes of the present invention are only very slowly removed from the bloodstream and thus have interesting properties for use as blood pool agents. Blood pool imaging is a very important tool, especially for examining the dynamic cardiological function, to gain an insight into the functioning of the heart. By using the cationic complexes of the present invention blood pool labelling can be achieved by a single injection procedure. Up to the present blood pool labelling is carried out by drawing blood from a patient, isolating blood cells, preferably erythrocytes, therefrom, labelling the blood cells and reinjecting the labelled blood cells; indeed a laborious procedure!

The following examples serve to illustrate the invention. Example I describes the preparation of complexes according to the invention, one process believed to be as shown in the following reaction scheme. Example II describes human experiments performed using the complexes of Example I.

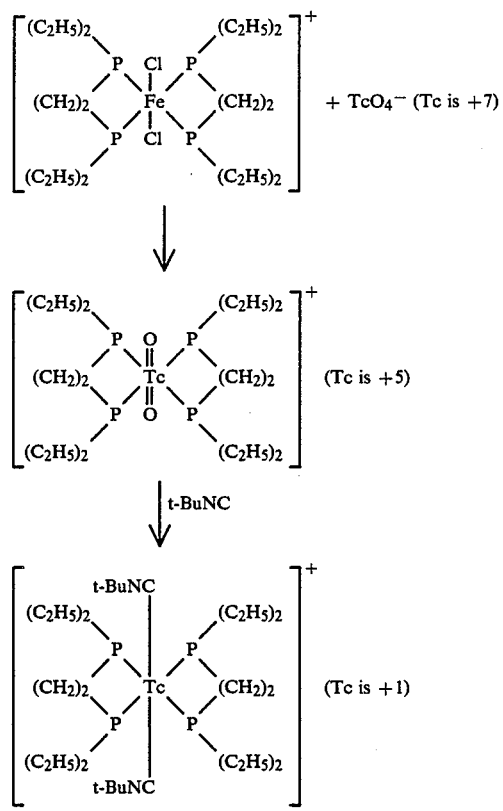

EXAMPLE I

Preparation of 1,2-bis(diethylphosphino)ethane tert.-butyl isocyanide cationic technetium-99m complex:

Reagents:
dichlorobis[1,2-bis(diethylphosphino)ethane]iron(III) chloride, [Fe(DEPE)$_2$Cl$_2$]Cl;
Ethylene glycol bis(aminoethyl ether)-N,N,N',N'-tetracetic acid, (EGTA);
sodium hyposulphite (Na$_2$S$_2$O$_4$);
0.2M hydrochloric acid;
0.2M sodium hydroxide;
p-aminobenzoic acid (PABA); and
t-butyl isocyanide.

Section 1: Procedure:

1. To 0.3 mg of EGTA (in a nitrogen filled, rubber capped, 10 ml multidose glass vial), is added 1 ml of $^{99m}$TcO$_4^-$/saline generator eluent and 50 μl of a 1 mg.ml$^{-1}$ solution of [Fe(DEPE)$_2$Cl$_2$]Cl in ethanol. The mixture is heated for 15 minutes in an oil bath held at 100° C.

2. The vial is allowed to cool and to stand at room temperature for 5 minutes; then is added 0.5 ml of 0.2M HCl, 0.5 ml of 30 mg.ml$^{-1}$ Na$_2$S$_2$O$_4$/H$_2$O (freshly prepared), and 0.5 ml of 30 mg.ml$^{-1}$PABA/H$_2$O. The vial is leaved standing at room temperature for 30 minutes. The pH at this stage is about 1.

3. To the vial is added 0.5 ml of 0.2M NaOH and 0.1 ml of 0.9M t-butyl isocyanide (in ethanol); the vial is heated for 5 minutes in an oil bath held at 100° C. The pH at this stage is about 4.

4. The vial is allowed to cool to room temperature and then the contents are passed through a sterile 0.2 μm millipore filter (Millex FG).

Section 2: HPLC Quality Control System:

Column: Hamilton PRP-1 Reversed Phase (25 cm×5 mm).

Eluent: 65% acetonitrile/35% 0.1M ammonium acetate, pH 6.8.

Flow Rate: 1 ml/min.

Using the above HPLC system, the final reaction mixture gives a single chromatographic peak with a retention time of ca. 11.5 minutes. Radiochemical purity is greater than 90%.

EXAMPLE II

By the same procedure as described in Example I above a complex with benzyl isocyanide instead of tert.-butyl isocyanide as the monodentate ligand is prepared. On HPLC this cationic complex gives a single chromatographic peak with a retention time of ca. 15.5 minutes (column and eluent as above). The radiochemical purity is greater than 95%.

In the same way cationic complexes according to the invention can be prepared wherein as the monodentate ligand isopropyl isocyanide is used and wherein as the bidentate ligand dimethylphosphinoethane and diphenylphosphinoethane instead of diethylphosphinoethane are used.

EXAMPLE III

The above complex of Example I is prepared as follows in a one-step procedure:

Into a 10 ml glass vial are added about 0.3 mg of EGTA, 15 mg of sodium dithionite, 10 mg of p-aminobenzoic acid as a stabiliser and 0.05 mg of [Fe(DEPE)$_2$Cl$_2$]Cl in 0.05 ml of ethanol. After closing the vial with a rubber cap and flushing with nitrogen 0.1 ml of 0.1M NaOH aqueous solution is added, mixed, followed by 0.1 ml of 0.9M tert.-butylisocyanide in ethanol and mixing. Then 1 ml of 99m-Tc as pertechnetate/saline generator eluent is added and mixed. The mixture is heated under pressure for 10 minutes and allowed to cool. The colourless liquid is subjected to the same HPLC procedure as described in Example I: retention time 11.5 minutes; radiochemical purities 91.5% and 93.3% (repetition).

EXAMPLE IV

Alternatively the above complexes according to the invention can be prepared by reacting the corresponding iron complexes, e.g. bis[1,2-bis(diethylphosphino)ethane]bis-(tert.-butyl isocyanide)iron(III) chloride, with technetium-99m in the form of sodium pertechnetate in saline solution in the presence of sodium hydroxide as a base and sodium dithionite as a reducing agent. The above iron(III) complexes can be prepared from dichlorobis[1,2-bis(diethylphosphino)ethane]iron(III) chloride, in substantially the same way as described Example I.

EXAMPLE IV

Procedure for multi-gated studies:

i. The imaging agent is injected into the right antecubital vein.

ii. The patient lies supine on the exercise couch with his feet on the pedals of an ergometric apparatus.

iii. 3-lead ECG electrodes are placed in the standard configuration on the patient and connected to the camera.

iv. The gamma camera is placed over the chest at 45° C. left anterior oblique with a 10° forward tilt. This aspect images mainly the left ventricle.

v. Imaging is started. The ECG electrodes are used to "gate" the camera so that it is active only during the cardiac R-cycle (left ventricular expansion and contraction).

vi. After collecting $5 \times 10^6$ counts, the computer is used to calculate left ventricular ejection fraction (LVEF) and left ventricular volume. The image of the pulsating left ventricle is visually analysed for qualitative asessment of possible left ventricular wall motion irregularities.

vii. The whole procedure is repeated after maximal exercise with the ergometric apparatus.

Comparison of the relative efficiencies of the product of Example I (Ex I) and $^{99m}$Tc-labelled red blood cells (RBC) for LVEF studies in normal human volunteers.

| Volunteer | Ejection fraction (%) | | KCPS/mCi | | mCi of Ex 1 injected |
|---|---|---|---|---|---|
| | Ex I | RBC | Ex 1 | RBC | |
| A (gamma camera) | 31 | 34 | 1.51 | 0.50 | 5.3 |
| A (gamma camera) | 32 | 31 | 1.64 | 0.72 | 5.5* |
| B (gamma camera) | 63 | 63 | 0.95 | 0.84 | 4.2 |
| C (gamma camera) | 52 | 50 | 1.54 | 0.80 | 4.2 |
| D (gamma camera) | 55 | 57 | 1.27 | 1.10 | 6.0 |
| A (nuclear stethoscope) | 34 | 35 | — | — | 5.5* |

Notes
i. The red blood cells were labelled by the "in vivo" method using a commercial RBC labelling kit.
ii. A portable "Elscint" gamma camera was used in all studies.
iii. A standard dose of 20 mCi of $^{99m}$Tc was used for RBC labelling.
iv. Average KCPS (kilocounts/second) for 20 patients, chosen at random, given 20 mCi of $^{99m}$Tc (in vivo RBC labelling) was 0.75.
*These two tests were carried out on the same day using the same injection.

The product of Example I thus gives LVEF information comparable to that given by the commercial RBC labelling kit, but with only a single injection (where two are needed for RBC kit) and using only 4-6 mCi of technetium-99m (where 20mCi are needed for the kit).

In the same way as described above the 1,2-bis(diethylphosphino)ethane benzyl isocyanide technetium-99m complex, prepared according to Example II, is tested in a human volunteer. Like the complex of Example I it remains in the blood pool and has similar kinetic characteristics as the complex of Example I.

We claim:
1. A cationic complex of technetium-99m with
   (a) at least one bidendate ligand X having the formula

$R_1R_2ZQZR_3R_4$ where
   each Z is phosphorus or arsenic,
   Q is a $(CH_2)_n$ linking group where n is 2 to 8 or a 1,2-phenylene linking group,
   each of $R_1$, $R_2$, $R_3$ and $R_4$ is hydrogen, $C_1$ to $C_5$ alkyl or phenyl; and
   (b) at least one monodentate isonitrile ligand Y.

2. A complex as claimed in claim 1, wherein Z is phosphorus, Q is $(CH_2)_2$, and $R_1$, $R_2$, $R_3$ and $R_4$ are all the same and are all methyl or ethyl.

3. A complex as claimed in claim 1 or claim 2, wherein Y is an aliphatic hydrocarbon isonitrile or benzyl isonitrile.

4. A complex as claimed in claim 1, having the structure $[Tc-99mX_2Y_2]^+$ wherein X and Y have the meanings given in claim 1.

5. A complex as claimed in claim 4, wherein Y has the meaning given in claim 3, and X is represented by the formula $R_1R_2ZQZR_3R_4$ wherein Z, Q, $R_1$, $R_2$, $R_3$ and $R_4$ have the meanings given in claim 2.

6. A radiopharmaceutical composition comprising in addition to a pharmaceutically acceptable, liquid carrier material a cationic complex of technetium-99m, characterized in that the composition comprises a complex as claimed in any of claims 1 to 5.

7. A method of performing a radiodiagnostic examination, in particular blood pool imaging, in a warm-blooded living being, characterized in that a composition as claimed in claim 6, is administered to the living being in a quantity from 0.1 to 50 mCi, per 70 kg of body weight, and the radioactive radiation emitted by the living being is then recorded.

* * * * *